United States Patent [19]
Arai et al.

[11] Patent Number: 4,577,041
[45] Date of Patent: Mar. 18, 1986

[54] CYCLIC ORGANOPOLYSILOXANE COMPOUND

[75] Inventors: Masatoshi Arai; Koji Futatsumori; Takeo Inoue; Shinichi Sato, all of Gunma, Japan

[73] Assignee: Shin-Etsu Chemical Co., Ltd., Tokyo, Japan

[21] Appl. No.: 749,174

[22] Filed: Jun. 26, 1985

[30] Foreign Application Priority Data

Jun. 29, 1984 [JP] Japan ................. 59-134175

[51] Int. Cl.$^4$ ............ C07F 7/04; C07F 7/08; C07F 7/18
[52] U.S. Cl. .................................. 556/446
[58] Field of Search .......................... 556/446

[56] References Cited

U.S. PATENT DOCUMENTS 4,098,808  7/1978  Wolfers et al. ............ 556/446

Primary Examiner—Paul F. Shaver
Attorney, Agent, or Firm—Toren, McGrady, Stanger, Goldberg & Kiel

[57] ABSTRACT

The invention provides a novel cyclic organopolysiloxane compound represented by the general formula

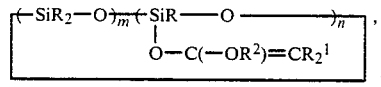

in which the groups denoted by R, $R^1$ and $R^2$ are each typically a monovalent hydrocarbon group having 1 to 8 carbon atoms, m is zero, 1, 2 or 3 and n is 2, 3 or 4 with the proviso that m+n is typically 4. A method for the preparation of the compound is disclosed. The inventive compound is useful as a crosslinking agent of a diorganopolysiloxane terminated at both molecular chain ends each with a silanolic hydroxy group so as to give a room temperature-curable silicone rubber composition free from the problem of emission of toxic or corrosive gases as a byproduct of the crosslinking reaction.

1 Claim, 8 Drawing Figures

CYCLIC ORGANOPOLYSILOXANE COMPOUND

BACKGROUND OF THE INVENTION

The present invention relates to a novel cyclic organopolysiloxane compound not known in the prior art or not described in any publications or, more particularly, the invention relates to a novel cyclic organopolysiloxane compound useful as a crosslinking agent in a room temperature-curable organopolysiloxane composition.

SUMMARY OF THE INVENTION

The novel cyclic organopolysiloxane compound provided by the present invention is represented by the general formula

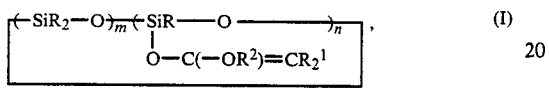  (I)

in which R is a group selected from the class consisting of halogenated or unhalogenated monovalent hydrocarbon groups having 1 to 8 carbon atoms and a trimethylsiloxy group, $R^1$ is a hydrogen atom or a substituted or unsubstituted monovalent hydrocarbon group having 1 to 8 carbon atoms, $R^2$ is a substituted or unsubstituted monovalent hydrocarbon group having 1 to 8 carbon atoms, m is zero, 1, 2 or 3 and n is 2, 3 or 4 with the proviso that m+n is 4 or 5.

DETAILED DESCRIPTION OF THE PREFERRED EMBODIMENTS

Figure 1:
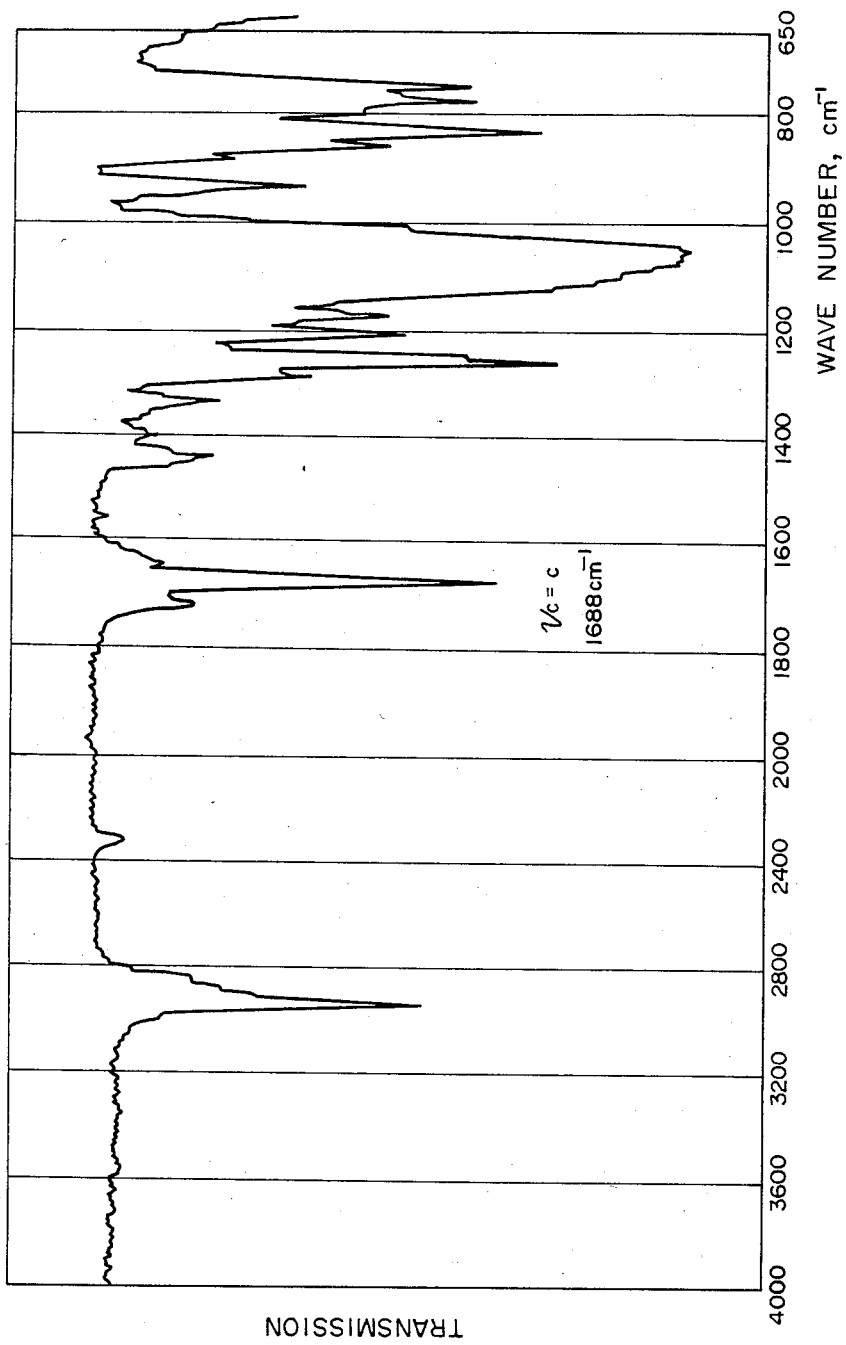
FIGS. 1 to 8 each show the infrared absorption spectrum of one of the inventive organopolysiloxane compounds prepared in Examples 1 to 8, respectively.

In the above description of the inventive organopolysiloxane compound, the symbols R, $R^1$ and $R^2$ each can denote a monovalent hydrocarbon group having 1 to 8 carbon atoms. Such a group is exemplified by alkyl groups, e.g. methyl, ethyl, propyl, butyl and cotyl groups, cycloalkyl groups, e.g. cyclohexyl and cyclopentyl groups, alkenyl groups, e.g. vinyl and allyl groups, aryl groups, e.g. phenyl, tolyl and xylyl groups, and aralkyl groups, e.g. benzyl and 2-phenylethyl groups. The halogenated monovalent hydrocarbon group, which may be denoted by R, is exemplified by chloromethyl, 3-chloropropyl and 3,3,3-trifluoropropyl groups.

Several of the particular examples of the inventive cyclic organopolysiloxane compound include those expressed by the following structural formulars A to I, in which the symbols of Me, Et, Pr, Bu and Oc denote methyl, ethyl, propyl, butyl and octyl groups, respectively, although the present invention is not limited thereto in any way.

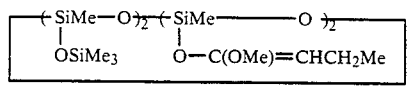 A

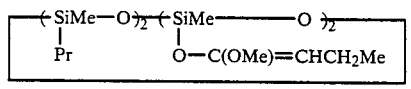 B

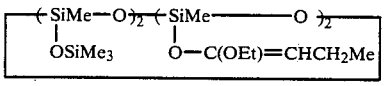 C

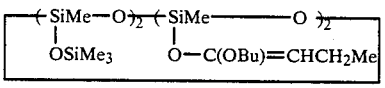 D

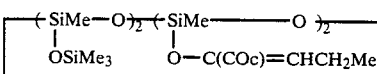 E

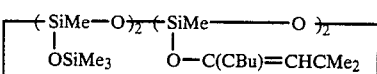 F

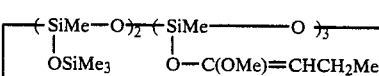 G

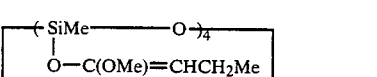 H

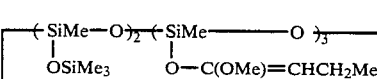 I

The most convenient method for the synthetic preparation of the inventive cyclic organopolysiloxane compound of the general formula (I) is as follows. That is, a cyclic organohydrogenpolysiloxane represented by the general formula

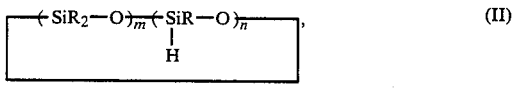  (II)

is subjected to a 1,4-addition reaction with an α,β-unsaturated ester compound represented by the general formula

  (III)

in which $R^1$ and $R^2$ each have the meaning as defined before and R' is an atom or group which makes $R'CH_2$— the same group as $R^1$, in the presence of a Wilkinson's catalyst which is a complex compound of rhodium of the formula $(Ph_3P)_3RhCl$, Ph being a phenyl group. The ratio of the unsaturated ester compound of the formula (III) to the cyclic organohydrogenpolysiloxane of the formula (II) in the reaction mixture in this case should be such that at least 1 mole or, preferably, from 1.1 to 1.2 moles of the unsaturated ester compound is provided per mole of the hydrogen atoms directly bonded to the silicon atoms in the cyclic polysiloxane. The reaction temperature is preferably in the range from 60° to 150° C. The reaction mixture may be diluted with an organic solvent such as benzene, toluene, xylene, hexane and the like.

The cyclic organopolysiloxane compound of the present invention is useful in various applications, of which the most important application is as a crosslinking agent of a diorganopolysilxane terminated at both molecular chain ends each with a silanolic hydroxy group as in the diorganopolysiloxane formulated in conventional room temperature-curable silicone rubber compositions widely used as a sealing and caulking material, coating material, electric insulating material and the like. The room temperature-curable silicone rubber composition formulated with the inventive cyclic organopolysiloxane compound as the crosslinking agent is free from the problem of emission of any toxic or corrosive gases formed as a byproduct of the crosslinking reaction.

In the following, preparation and characterization of several of the cylic organopolysiloxane compounds according to the invention are described in more detail by way of examples which should not be construed as limiting in any way.

EXAMPLE 1

Into a three-necked flask of 50 ml capacity equipped with a reflux condenser, thermometer and dropping funnel were introduced 9.8 g of 1,3,5,7-tetramethyl-1,5-bis(trimethylsiloxy)cyclotetrasiloxane, 9.4 g of methyl crotonate and 0.01 g of chloro tris(triphenylphosphine)rhodium and the reaction mixture was agitated for 4 hours at 90° C. by use of an electromagnetic stirrer. After completion of the reaction, low volatile matters were removed from the reaction mixture by distillation to give 14.2 g of a reaction product having a refractive index of 1.421 at 25° C., which was identified to be the cyclic organopolysiloxane of the formula A given before from the results of the infrared absorption spectroscopy (see the spectrum shown in FIG. 1), NMR analysis and elementary analysis given below. The above mentioned yield of the product was 97.7% of the theoretical value.

NMR data: 0.31 (s, Si—$CH_3$, 3OH), 1.06 (t, C—$CH_3$, 6H), 2.00 (q, C—$CH_2$, 4H), 3.60 (s, O—$CH_3$, 6H)

| Elementary analysis: | C, % | H, % | Si, % |
|---|---|---|---|
| Calculated as $C_{20}H_{48}O_{10}Si_6$ | 38.9 | 7.8 | 27.3 |
| Found | 39.1 | 7.6 | 27.0 |

EXAMPLE 2

Figure 2:
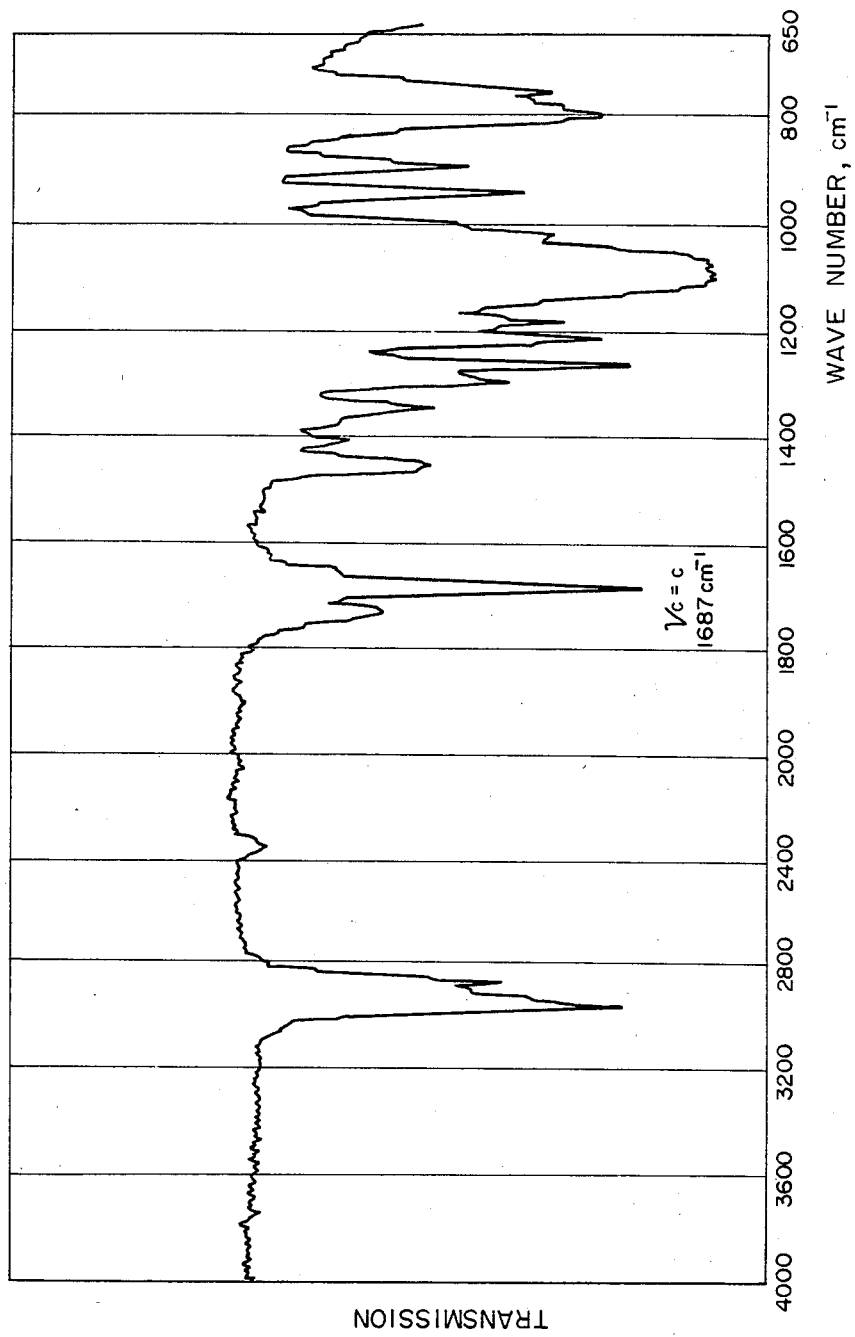

The reaction was performed in a similar manner to Example 1 with a reaction mixture composed of 19.6 g of 1,3,5,7-tetramethyl-1,5-dipropyl cyclotetrasiloxane, 12.6 g of methyl crotonate and 0.01 g of the same rhodium complex as used in Example 1 to give 30.6 g of a reaction product having a refractive index of 1.433 at 25° C., which could be identified to be the cyclic organopolysiloxane of the formula B given before from the results of the infrared absorption spectroscopy (see the spectrum shown in FIG. 2), NMR analysis and elementary analysis given below. The above mentioned yield of the product was 97.6% of the theoretical value.

NMR data: 0.29 (s, Si—$CH_3$, 12H), 1.10 (t, C—$CH_3$, 6H), 1.98 (q, C—$CH_2$, 4H), 3.59 (s, O—$CH_3$, 6H)

| Elementary analysis: | C, % | H, % | Si, % |
|---|---|---|---|
| Calculated as $C_{20}H_{44}O_8Si_4$ | 45.8 | 8.4 | 21.4 |
| Found | 45.7 | 8.5 | 21.1 |

EXAMPLE 3

Figure 3:
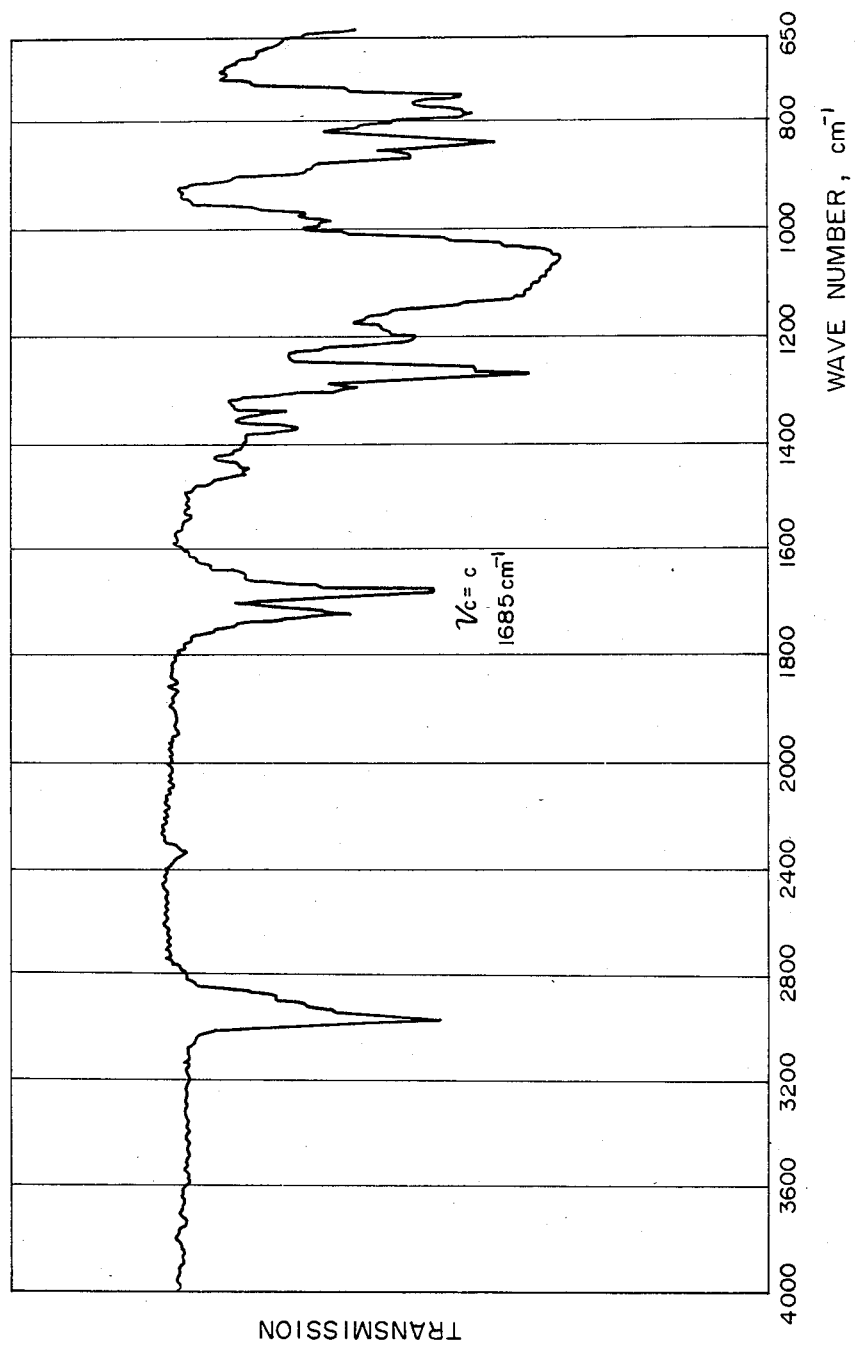

The reaction was performed in a similar manner to Example 1 with a reaction mixture composed of 9.7 g of 1,3,5,7-tetramethyl-1,5-bis(trimethylsiloxy)cyclotetrasiloxane, 9.6 g of ethyl crotonate and 0.01 g of the same rhodium complex as in Example 1 to give 15.0 g of a reaction product having a refractive index of 1.420 at 25° C., which could be identified to be the cyclic organopolysiloxane of the formula C given before from the results of the infrated absorption spectroscopy (see the spectrum shown in FIG. 3), NMR analysis and elementary analysis given below. The above mentioned yield of the product was 99.7% of the theoretical value.

NMR data: 0.31 (s, Si—$CH_3$, 3OH), 1.08 (t, C—$CH_3$, 6H), 2.03 (q, C—$CH_2$, 4H), 3.91 (q, O—$CH_2$, 4H),

| Elementary analysis: | C, % | H, % | Si, % |
|---|---|---|---|
| Calculated as $C_{22}H_{52}O_{10}Si_6$ | 41.0 | 8.1 | 26.1 |
| Found | 41.3 | 7.9 | 25.9 |

EXAMPLE 4

Figure 4:
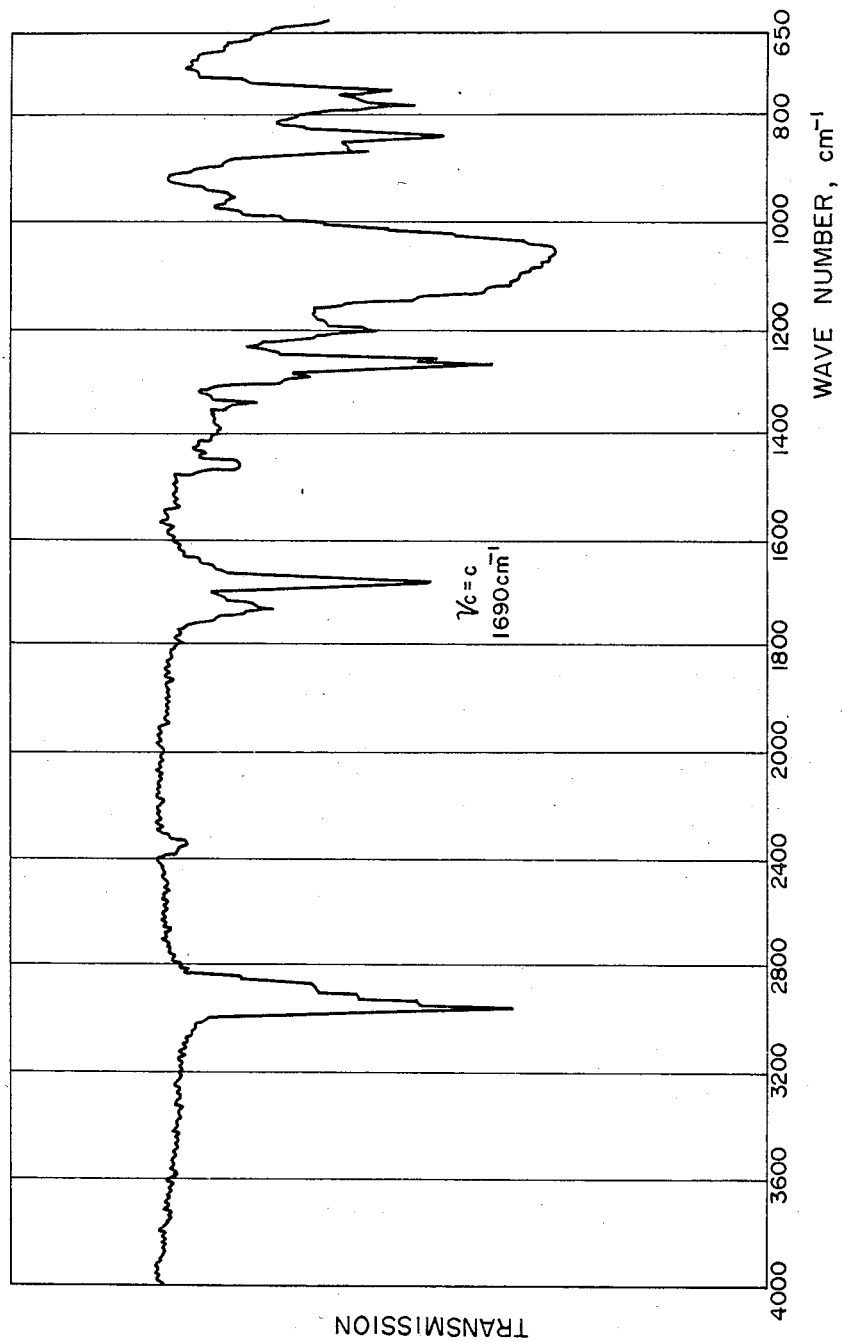

The reaction was performed in a similar manner to Example 1 with a reaction mixture composed of 10.4 g of 1,3,5,7-tetramethyl-1,5-bis(trimethylsiloxy)cyclotetrasiloxane, 7.2 g of butyl crotonate and 0.01 g of the same rhodium complex as in Example 1 to give 16.2 g of a reaction product having a refractive index of 1.424 at 25° C., which could be identified to be the cyclic organopolysiloxane of the formula D given before from the results of the infrared absorption spectroscopy (see the spectrum shown in FIG. 4), NMR analysis and elementary analysis given below. The above mentioned yield of the product was 92.6% of the theoretical value.

NMR data: 0.30 (s, Si—$CH_3$, 3OH), 1.06 (t, C—$CH_3$, 6H), 2.02 (t, C—$CH_2$, 4H), 3.86 (t, C—$CH_2$, $H)

| Elementary analysis: | C, % | H, % | Si, % |
|---|---|---|---|
| Calculated as $C_{26}H_{60}O_{10}Si_6$ | 44.5 | 8.6 | 24.0 |
| Found | 44.4 | 8.5 | 24.3 |

EXAMPLE 5

Figure 5:
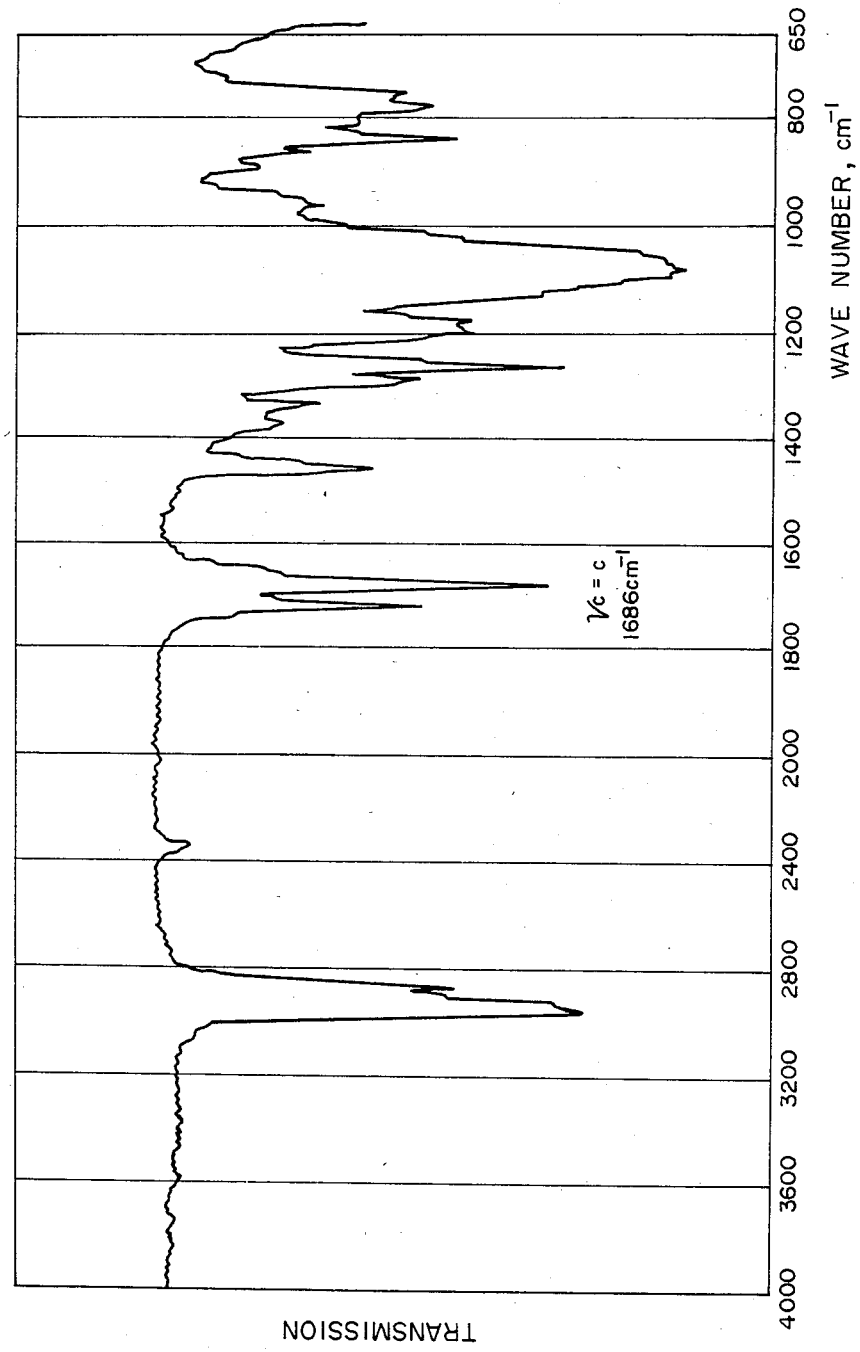

The reaction was performed in a similar manner to Example 1 with a reaction mixture composed of 10.4 g of 1,3,5,7-tetramethyl-1,5-bis(trimethylsiloxy)cyclotetrasiloxane, 15.3 g of 2-ethylhexyl crotonate and 0.01 g of the same rhodium complex as in Example 1 to give 17.5 g of a reaction product having a refractive index of 1.432 at 25° C., which could be identified to be the cyclic organopolysiloxane of the formula E given before from the results of the infrared absorption spectroscopy (see the spectrum shown in FIG. 5), NMR analysis and elementary analysis given below. The above mentioned yield of the product was 86% of the theoretical value.

NMR data: 0.25 (s, Si—$CH_3$, 3OH), 0.8 to 1.7 (m, Oct, 3OH), 2.00 (q, =C—$CH_2$, 4H), 3.75 (t, O—$CH_2$, 4H)

| Elementary analysis: | C, % | H, % | Si, % |
|---|---|---|---|
| Calculated as $C_{34}H_{76}O_{10}Si_6$ | 50.2 | 9.4 | 20.7 |
| Found | 50.0 | 9.3 | 20.8 |

EXAMPLE 6

Figure 6:
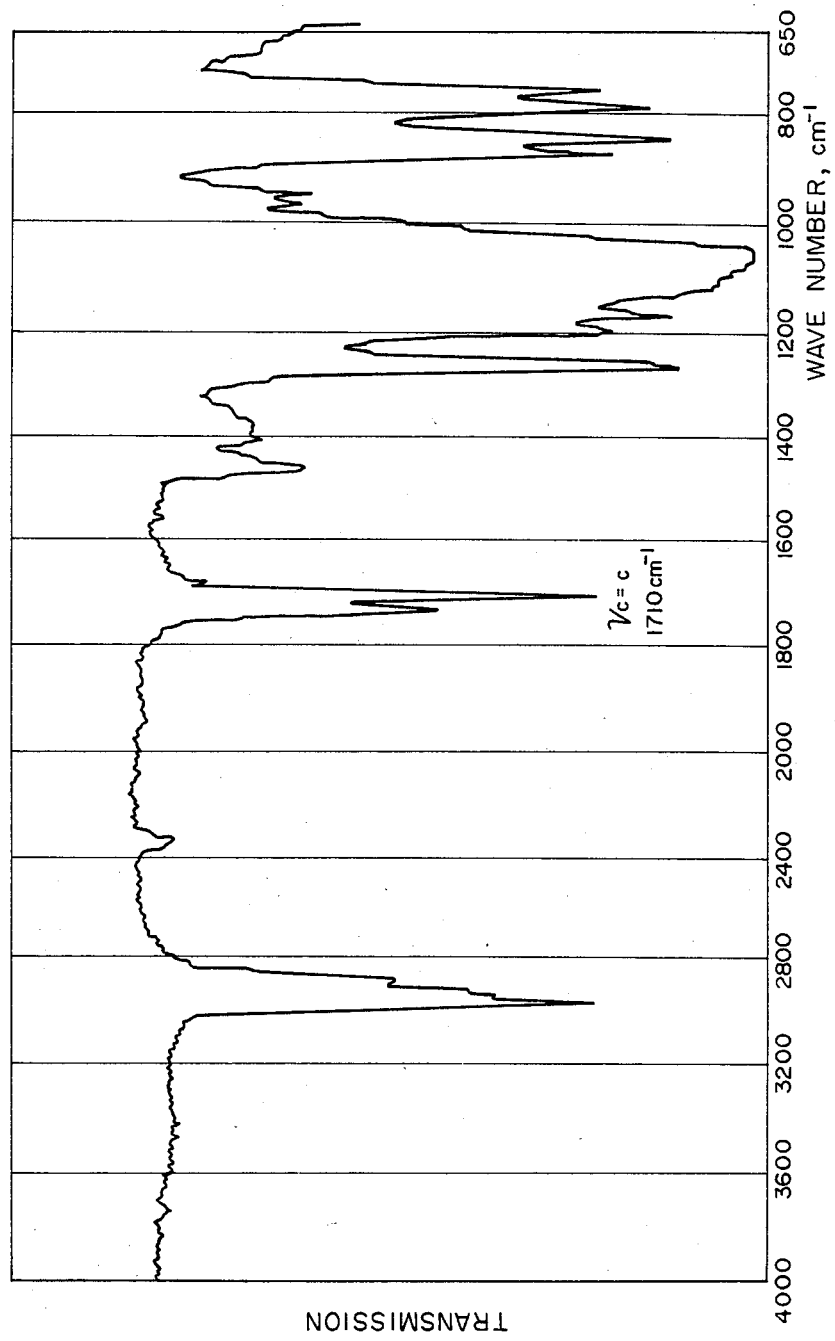

The reaction was performed in a similar manner to Example 1 with a reaction mixture composed of 10.4 g of 1,3,5,7-tetramethyl-1,5-bis(trimethylsiloxy)cyclotetrasiloxane, 7.3 g of n-butyl methacrylate and 0.01 g of the same rhodium complex as in Example 1 to give 17.0 g of a reaction product having a refractive index of 1.426 at 25° C., which could be identified to be a cyclic organopolysiloxane of the formula F given before from the results of the infrared absorption spectroscopy (see the spectrum shown in FIG. 6), NMR analysis and elementary analysis given below. The above mentioned yield of the product was 97.0% of the theoretical value.

NMR data: 0.28 (s, Si—$CH_3$, 3OH), 0.9 to 1.5 (m, Bu, 14H), 1.66 (s, =C—C—$CH_3$, 12H), 3.78 (t, O—$CH_2$, 4H)

| Elementary analysis: | C, % | H, % | Si, % |
| --- | --- | --- | --- |
| Calculated as $C_{26}H_{60}O_{10}Si_6$ | 44.5 | 8.6 | 24.0 |
| Found | 44.6 | 8.3 | 23.8 |

EXAMPLE 7

Figure 7:
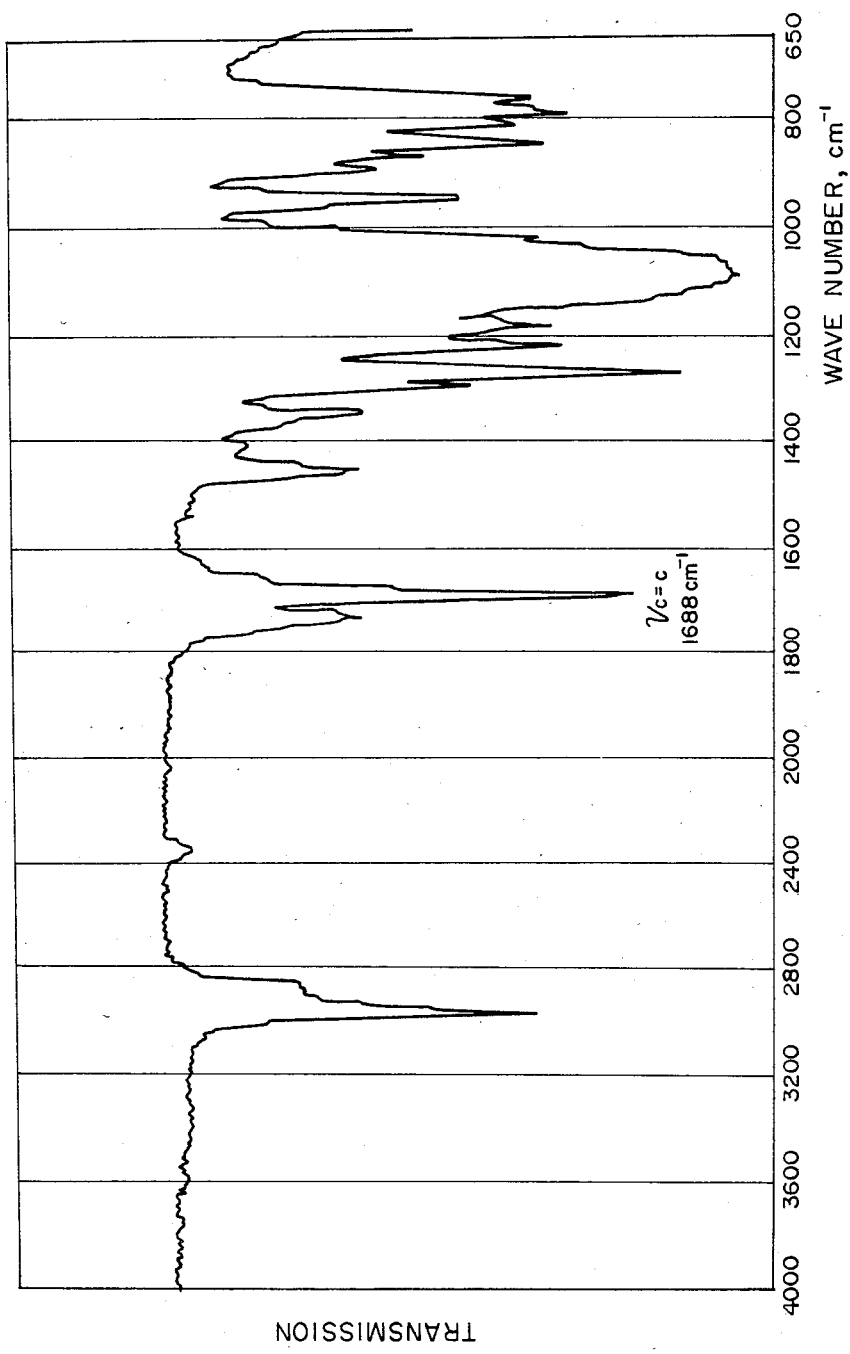

The reaction was performed in a similar manner to Example 1 with a reaction mixture composed of 8.7 g of 1,3,5,7-tetramethyl trimethylsiloxy cyclotetrasiloxane, 10.3 g of methyl crotonate and 0.01 g of the same rhodium complex as in Example 1 to give 15.6 g of a reaction product having a refractive index of 1.431 at 25° C., which could be identified to be the cyclic organopolysiloxane of the formula G given before from the results of the infrared absorption spectroscopy (see the spectrum shown in FIG. 7), NMR analysis and elementary analysis given below. The above mentioned yield of the product was 97.9% of the theoretical value.

NMR data: 0.28 (s, Si—$CH_3$, 21H), 1.05 (t, C—$CH_3$, 9H), 1.99 (q, C—$CH_2$, 6H), 3.60 (s, O—$CH_3$, 9H)

| Elementary analysis: | C, % | H, % | Si, % |
| --- | --- | --- | --- |
| Calculated as $C_{22}H_{48}O_{11}Si_5$ | 42.0 | 7.7 | 22.3 |
| Found | 41.7 | 7.8 | 22.4 |

EXAMPLE 8

Figure 8:
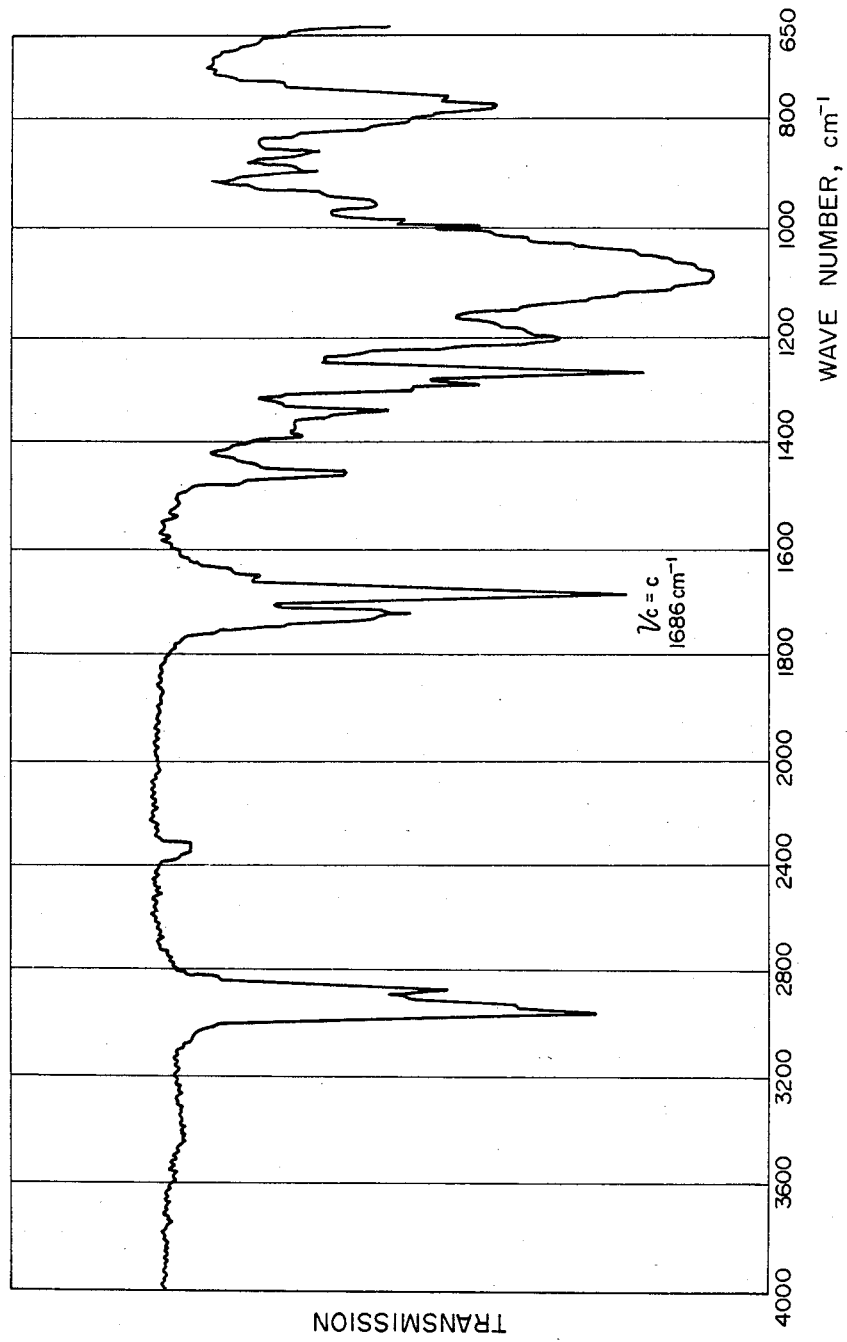

The reaction was performed in a similar manner to Example 1 with a reaction mixture composed of 4.8 g of 1,3,5,7-tetramethyl cyclotetrasiloxane, 11.8 g of butyl crotonate and 0.01 g of the same rhodium complex as in Example 1 to give 15.8 g of a reaction product having a refractive index of 1.442 at 25° C., which could be identified to be the cyclic organopolysiloxane of the formula H given before from the results of the infrared absorption spectroscopy (see the spectrum shown in FIG. 8), NMR analysis and elementary analysis given below. The above mentioned yield of the product was 97.6% of the theortical value.

NMR data: 0.40 (s, Si—$CH_3$, 12H), 0.8 to 1.9 (m, Bu, 28H), 1.98 (q, C—$CH_2$, 8H), 3.79 (s, O—$CH_2$, 8H)

| Elementary analysis: | C, % | H, % | Si, % |
| --- | --- | --- | --- |
| Calculated as $C_{36}H_{72}O_{12}Si_4$ | 53.4 | 9.0 | 13.9 |
| Found | 53.2 | 8.8 | 14.1 |

What is claimed is:

1. A cyclic organopolysiloxane compound represented by the general formula

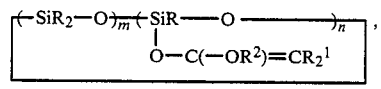

in which R is a group selected from the class consisting of halogenated or unhalogenated monovalent hydrocarbon groups having 1 to 8 carbon atoms and a trimethylsiloxy group, $R^1$ is a hydrogen atom or a substituted or unsubstituted monovalent hydrocarbon group having 1 to 8 carbon atoms, $R^2$ is a substituted or unsubstituted monovalent hydrocarbon group having 1 to 8 carbon atoms, m is zero, 1, 2 or 3 and n is 2, 3 or 4 with the proviso that m+n is 4 or 5.

* * * * *